(12) United States Patent
Fjerdingstad

(10) Patent No.: US 8,424,397 B2
(45) Date of Patent: Apr. 23, 2013

(54) PARTICLE COUNTER APPARATUS

(75) Inventor: Sølve Fjerdingstad, Ås (NO)

(73) Assignee: Fras Technology AS, Ovre Ardal (NO)

( * ) Notice: Subject to any disclaimer, the term of this patent is extended or adjusted under 35 U.S.C. 154(b) by 721 days.

(21) Appl. No.: 12/530,926

(22) PCT Filed: Mar. 14, 2008

(86) PCT No.: PCT/NO2008/000100
§ 371 (c)(1),
(2), (4) Date: Mar. 3, 2010

(87) PCT Pub. No.: WO2008/111851
PCT Pub. Date: Sep. 18, 2008

(65) Prior Publication Data
US 2010/0180700 A1 Jul. 22, 2010

(30) Foreign Application Priority Data
Mar. 14, 2007 (NO) .................................. 20071390

(51) Int. Cl.
G01N 1/20 (2006.01)
G01N 1/14 (2006.01)
G01N 15/02 (2006.01)
G01N 15/14 (2006.01)

(52) U.S. Cl.
USPC ... 73/865.5; 73/61.71; 73/863.02; 73/863.61; 73/863.86

(58) Field of Classification Search .................. 73/28.01, 73/61.71, 863.02–863.03, 863.43, 863.61–863.71, 73/863.86, 864.51, 864.63
See application file for complete search history.

(56) References Cited

U.S. PATENT DOCUMENTS

| 2,906,126 A | | 9/1959 | Brown | |
|---|---|---|---|---|
| 2,940,302 A | | 6/1960 | Scherbatskoy | |
| 3,282,113 A | * | 11/1966 | Sachnik | 73/863.02 |
| 3,504,549 A | * | 4/1970 | Davis et al. | 73/863.61 |
| 3,538,748 A | * | 11/1970 | Linsell et al. | 73/863.61 X |
| 3,538,768 A | * | 11/1970 | Duncan | 73/863.61 X |

(Continued)

FOREIGN PATENT DOCUMENTS

| EP | 31317 A1 * 7/1981 | 73/198 |
|---|---|---|
| EP | 41825 A1 * 12/1981 | |

(Continued)

OTHER PUBLICATIONS

International Search Report from the European Patent Office in International Application No. PCT/NO2008/000100, dated Jul. 15, 2008.

Primary Examiner — Thomas P Noland
(74) Attorney, Agent, or Firm — Finnegan, Henderson, Farabow, Garrett & Dunner, L.L.P.

(57) ABSTRACT

The invention relates to a particle counter apparatus for counting particles in a fluid flowing in a pipe or a pipeline. The particle counter apparatus comprises a pipe portion through which the fluid flows, where the pipe portion is provided with a fluid sample outlet for withdrawal of a fluid sample. Furthermore the particle counter apparatus also comprises a first fluid transfer body extending from the fluid sample outlet to a particle counter, and a second fluid transfer body extending from the particle counter to a fluid return outlet mounted in the pipe portion downstream of the fluid sample outlet. In the pipe portion there is mounted a propeller unit comprising a propeller and a generator, with the result that particles are distributed uniformly in the fluid before the withdrawal of fluid samples, and electric power is provided for operation of the particle counter apparatus.

17 Claims, 2 Drawing Sheets

U.S. PATENT DOCUMENTS

Figures 1, 2:
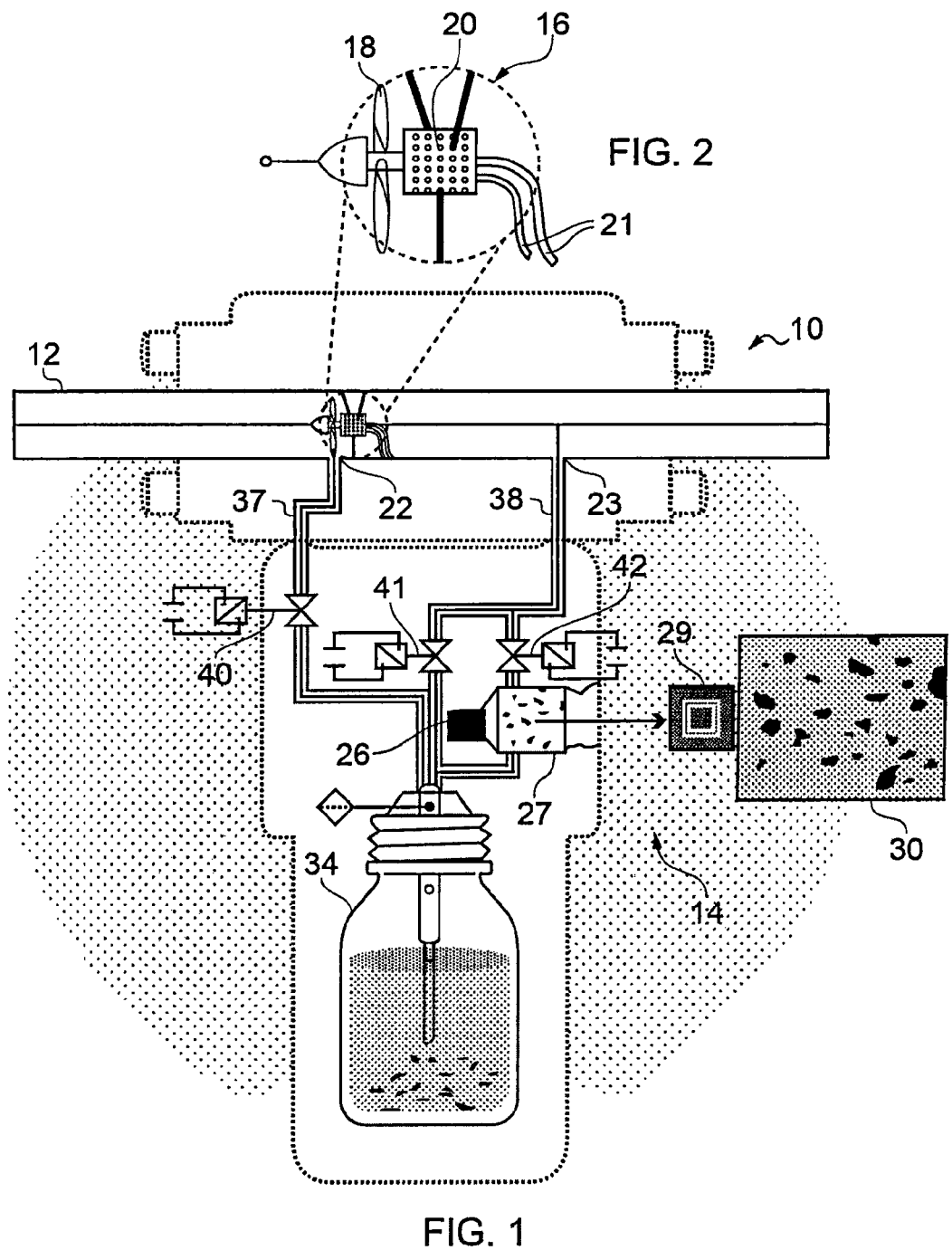

| | | | |
|---|---|---|---|
| 3,681,997 A * | 8/1972 | Allen et al. | 73/863.61 |
| 4,307,620 A | 12/1981 | Jiskoot | |
| 4,325,014 A * | 4/1982 | Jeck | 318/614 |
| 4,679,448 A | 7/1987 | Lund | |
| 5,413,002 A | 5/1995 | Jiskoot et al. | |
| 5,763,794 A * | 6/1998 | Marrelli | 73/863.02 |
| 6,742,404 B2 | 6/2004 | Smith et al. | |
| 2002/0166391 A1 * | 11/2002 | Khan et al. | 73/863.61 |
| 2004/0112150 A1 * | 6/2004 | Germond | 73/863.21 |
| 2004/0197922 A1 | 10/2004 | Cooper | |
| 2010/0089173 A1 * | 4/2010 | Verdier et al. | 73/863.21 X |
| 2011/0214511 A1 * | 9/2011 | Fjerdingstad | 73/861.41 |

FOREIGN PATENT DOCUMENTS

| | | | |
|---|---|---|---|
| EP | 75977 A * | | 4/1983 |
| FR | 2 653 554 | | 4/1991 |
| GB | 1 450 032 | | 9/1976 |
| GB | 2 164 021 A | | 3/1986 |
| GB | 2357710 A * | | 7/2001 |
| GB | 2425971 A * | | 11/2006 |
| JP | 2002-267510 | | 9/2002 |
| WO | WO 91/08467 | | 6/1991 |
| WO | WO 2004/057306 A1 | | 7/2004 |

* cited by examiner ial. Preferably the propeller is located immediately upstream of the fluid sample outlet. This ensures that the fluid sample is taken out near the propeller where the particles are best distributed.

PARTICLE COUNTER APPARATUS

FIELD OF THE INVENTION

The present invention relates to a particle counter apparatus for counting particles in a fluid flowing in a pipe or in a pipeline. The present invention also relates to use of the particle counter apparatus.

BACKGROUND OF THE INVENTION

The particle counter apparatus is particularly intended for use in counting particles in a fluid flowing in a pipe or a pipeline located in areas with difficult access such as for example on an ocean or sea bed. This may involve hydrocarbons flowing preferably in a pipe or a pipeline which may form a part of subsea production equipment or a pipeline for transport of hydrocarbons from the production equipment to land or interim storage in an installation at or below the surface. The invention may also be employed in areas where there is a risk of explosion and/or fire.

When the number of particles present in a fluid has to be counted, the particles should be as uniformly distributed in the fluid as possible. Should the particles for some reason or other have a tendency to agglomerate in the fluid, it could give an entirely false picture of the particle density in the fluid if the fluid sample removed for counting particles either contains fluid with a particle density which is below or above the real particle density in the fluid. It is therefore advantageous to mix the fluid in order to obtain a uniform distribution of particles in the fluid before a fluid sample is removed for counting particles in the fluid.

From the prior art it is known from EP 75977 A2 to install a static mixer in a mixing zone in a pipeline for mixing a fluid flowing in the pipeline. The mixing zone is provided some distance upstream of the outlet for fluid samples and comprises slanting blades on the inside of the pipeline which cause the fluid to acquire a rotating motion. According to the description, the intake for the fluid sample must not be placed in the wake of the mixer. The intake must therefore be understood to be located a good distance downstream of the mixer. A similar static mixer is also disclosed in EP 41825 A1, which is made for use in unloading systems for unloading oil from a vessel. Samples are taken in order to check the quality of the oil. None of these systems are arranged so that there is a pressure drop in the pipeline between drawing fluid from and return of fluid to the pipe flow. The fluid samples therefore have to be pump-driven.

Another method of mixing fluids is disclosed, for example, in GB 2 357 710 A, GB 2 164 021 A and U.S. Pat. No. 4,307,620, where the fluid sample removed for analysis is injected into the pipe flow upstream of the outlet for the fluid sample. The injection of the fluid sample should then cause the fluid in the pipe flow to be mixed. This requires continuous injection of fluid into the pipe flow, and possibly an accurately controlled injection of a sample in relation to tapping a new sample. All these devices require a pump in order to pump the fluid which has to be injected into the pipe flow.

A further method of mixing fluid is disclosed in GB 2 425 971 A, where a portion of a pipe or a pipeline is equipped with one or more bends in order to mix the fluid.

In WO 2004/057306 A1, which is the applicant's own patent application, a particle counter is disclosed for counting particles in a fluid sample removed from a fluid pipe flow. This application, however, relates to the particle counter as such and no mention is made of how electric power can be provided when the particle counter has to be used for investigation of fluid pipe flows in pipes or pipelines in areas with difficult access, such as for example pipes and pipelines located in deep water or in areas where there is a risk of fire and/or explosion. Nor is there any mention of how to obtain a mixing of the pipe flow, thereby causing any particles in the pipe flow to be uniformly distributed before a fluid sample is removed for analysis.

Since the present particle counter apparatus is intended for use in an environment which is difficult of access or in surroundings where there is a risk of fire and/or explosion, it is also an advantage for the particle counter to be entirely or to the greatest possible extent self-sufficient in the energy required. This avoids the use of cables for supplying electric energy for operating the particle counter. Electric cables will constitute a safety risk in areas where there is a risk of fire and/or explosion and in deep water it is a disadvantage to have to lay cables from the surface to equipment located below the surface. In other ways too it is an advantage if the whole particle counter apparatus can function as far as possible without external intervention or supply of electric power or other energy. This applies, for example, to the light source for particle counting and image recognition, data processing, cable-free communication for transmitting data from the particle counter and/or control signals for controlling the particle counter and other parts of the particle counter apparatus.

SUMMARY OF THE INVENTION

The object of the present invention is to provide a particle counter apparatus which fulfils these requirements.

This object is achieved with a particle counter apparatus as defined in the independent claim 1, and by methods for counting particles with such a particle counter apparatus as indicated in claims 16 and 17. Further preferred embodiments of the particle counter apparatus are indicated in the associated dependent claims 2-15.

A particle counter apparatus is provided for counting particles in a fluid flowing in a pipe or a pipeline, where the particle counter apparatus comprises a pipe portion through which the fluid flows and which is provided with a fluid sample outlet for withdrawing a fluid sample. The particle counter apparatus also comprises a first fluid transfer body extending from the fluid sample outlet to a particle counter, and a second fluid transfer body extending from the particle counter to a fluid return outlet mounted in the pipe portion downstream of the fluid sample outlet. The particle counter apparatus further comprises a propeller unit with a propeller, which is mounted in the pipe portion, either directly opposite the fluid sample outlet or upstream of the fluid sample outlet, with the result that solid particles are distributed in the fluid before withdrawal of a fluid sample. The propeller unit further comprises a generator driven by the propeller and means for transmitting electrical energy to the particle counter, thereby enabling the propeller unit to provide the particle counter with sufficient electric power to operate the particle counter.

The particle counter apparatus further comprises a pressure-reducing valve mounted in the pipeline between the first pipe branching and the second pipe branching, thereby permitting a pressure drop to be provided in the pipe flow which is sufficient to drive a fluid sample through the particle counter. This avoids the necessity of using a pump, which requires an energy supply to enable it to work, in order to drive the fluid sample through the particle counter and back to the pipe portion.

As mentioned above, the propeller unit may be located slightly upstream of the fluid sample outlet. In this case this distance is preferably less than twice the length of the propeller unit measured in the pipe portion's longitudinal axis when the propeller unit is installed in the pipe portion.

Since it has been an object of the present invention to make it as independent as possible of an external electrical energy supply, preferably completely independent of an electric power supply, in a preferred embodiment the propeller unit is provided with a unit for generating electric current. This propeller unit is driven by the propeller which in turn is driven by the fluid flowing through the pipe portion. The particle counter apparatus further comprises means, preferably in the form of electric cables, for transmitting the electric current produced by the propeller unit from the propeller unit to the particle counter. The electrical energy produced is preferably used for operating necessary functions of the actual particle counter and functions related to the particle counter and possibly control of the flow of fluid samples through the particle counter apparatus.

The particle counter apparatus may be employed in areas which are inaccessible for manual sampling, and for that reason the particle counter preferably comprises means for automatic counting of particles in the particle counter. To express it in simple terms, such equipment may, for example, comprise a laser diode which transilluminates a sample, a magnifying lens arrangement through which the laser light passes and a sensor, for example a camera, which records images for subsequent analysis.

The particle counter further comprises at least one data storage unit which can store data from the analysis concerning each individual fluid sample or image.

In order to gain access to data recorded for the fluid samples, the particle counter apparatus comprises means for transmitting data and any control signals between the particle counter and a receiver located at a distance from the particle counter apparatus. Particularly when the particle counter apparatus is used in areas with difficult access, such as for example in an underwater environment, or when used in an environment where there is a risk of fire and/or explosion, the particle counter apparatus preferably comprises means for transmitting data where the means comprise one or more devices for wireless transmission of data. It will also be possible to control the individual parts of the particle counter apparatus, such as valves, by means of control signals transmitted between the particle counter apparatus and the receiver. The signals transmitted between the particle counter apparatus and the receiver are preferably transmitted by means of the wireless transmitter/receiver means. Systems for wireless transmission of data and/or signals constitute well-known technology and will not be further discussed in this application.

Where it is not possible or desirable to employ a wireless system for transmission of data and/or control signals to and from the particle counter apparatus, one or more cables may preferably be used for transmitting data and/or control signals between the particle counter apparatus and the receiver.

In addition to the automatic arrangement for particle counting mentioned above, the particle counter also comprises one or more sample containers which can collect one or more fluid samples, thereby enabling the number of particles in the fluid sample to be counted in a suitable laboratory. This may be relevant if data from the automatic count differs from the values anticipated. The sample containers are preferably releasably mounted in the particle counter in such a manner that the sample container can be removed from and placed in the particle counter by an ROV, a robot or similar equipment. This may be implemented, for example, by means of a rapid coupling which is known in the prior art.

In an embodiment of the particle counter apparatus, the fluid sample outlet or the first fluid transfer body comprises means for withdrawing a predetermined amount of fluid. Such means may, for example, comprise one or more valves. In addition, the particle counter apparatus may be provided with additional valves for regulating the flow of fluid through the particle counter. The valves are preferably automatic. How great an amount should be removed from the fluid stream through the pipe portion at any time can be regulated by means of the wireless particle counter apparatus or the above-mentioned cables. This regulation may also be carried out by setting the means manually.

In order to prevent backflow of fluid from the pipe portion into the second fluid transfer body, the fluid return outlet preferably comprises means for preventing such backflow. Such means will preferably comprise a non-return valve or another suitable valve device.

In practical use the pipe portion will form a part of a pipe or a pipeline for transport of a fluid and the particle counter apparatus will be used to perform counting of particles in the fluid. The fluid samples may be removed at fixed, regular intervals or one or more samples may be removed when required by sending instructions to the particle counter apparatus via wireless transmission or through signal cables as described above.

The present invention also relates to a use of the particle counter apparatus as described above for transport of hydrocarbons in a pipe or a pipeline where the pipe portion forms a part of the pipe or the pipeline.

The present invention further comprises a use of a particle counter apparatus as described above for counting particles in a fluid pipe flow in a pipe or a pipeline where the fluid pipe flow comprises hydrocarbons, and where the pipeline is located under water or in an environment where there is a risk of fire and/or explosion.

An embodiment of the invention will now be described in greater detail with reference to the attached figures, in which

BRIEF DESCRIPTION OF THE DRAWING FIGURES

Figures 3, 4:
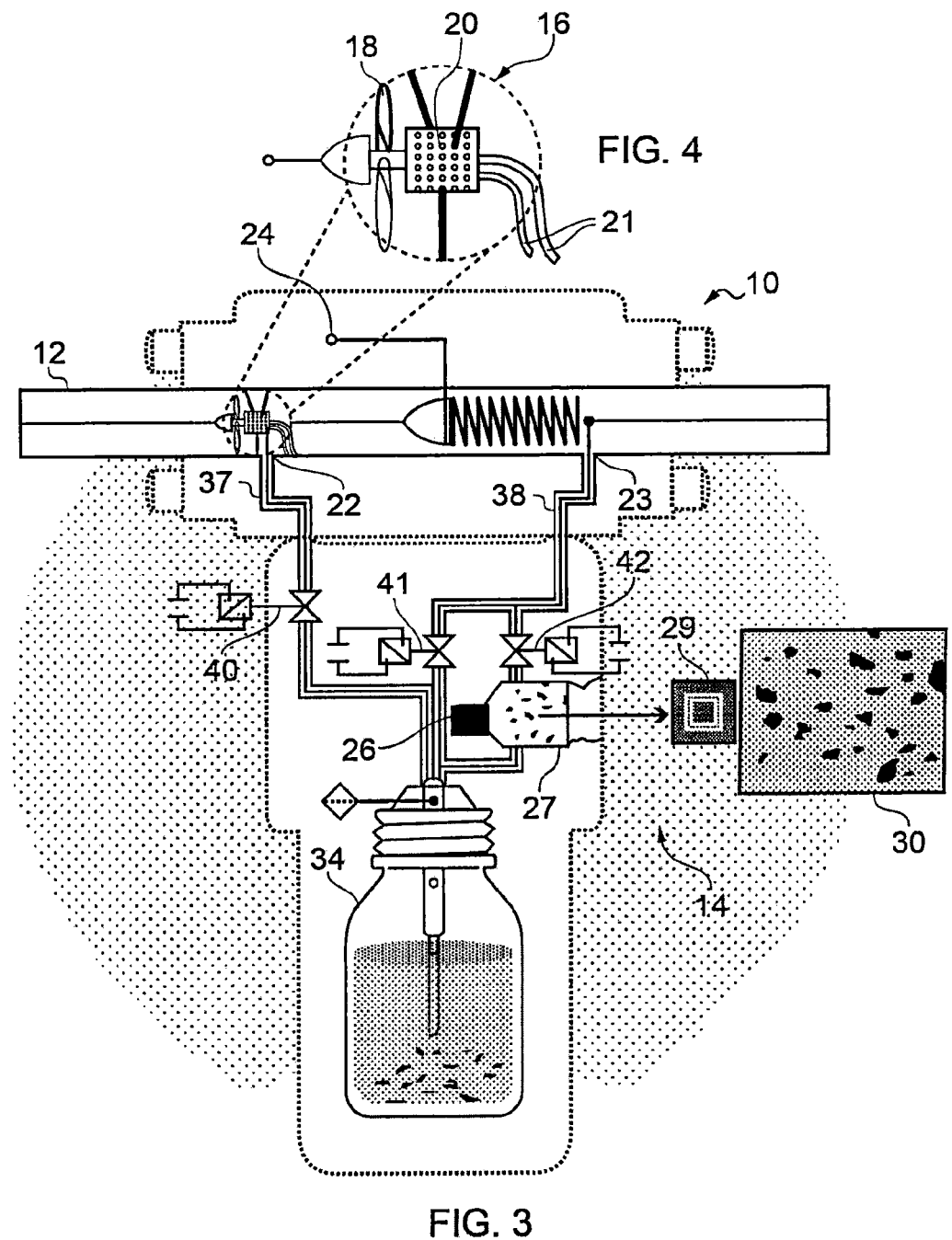

FIG. 1 is a schematic view of the invention according to a first aspect of the invention, FIG. 2 is a schematic view of the propeller unit in an enlarged version, FIG. 3 is a schematic view of the invention according to a second aspect of the invention, FIG. 4 is a schematic view of the propeller unit in an enlarged version.

DETAILED DESCRIPTION

FIGS. 1 and 2 illustrate the particle counter apparatus 10 for particle counting. The particle counter apparatus 10 comprises a pipe portion 12, which, when the particle counter apparatus 10 is in use, forms a part of a pipe or a pipeline in which a fluid is flowing. In the pipe portion 12 is provided a fluid sample outlet 22 and downstream of the fluid sample outlet 22, a fluid return outlet 23. From the fluid sample outlet 22 there is connected a first fluid transfer body 37 extending up to a particle counter, indicated generally as 14 in the figures. From the particle counter 14 there extends a second fluid transfer body 38 which returns fluid to the pipe portion 12 through a fluid return outlet 23. The fluid transfer bodies 37, 38 may comprise pipes, hoses or other suitable means for transferring the fluid. In the fluid transfer bodies 37, 38 furthermore, there are provided one or more valves 40, 41, 42, which are preferably automatic valves. The valves 40, 41, 42 control withdrawal of fluid samples from the fluid flow in the pipe portion 12 and the flow of fluid through the particle counter 14 back to the pipe portion 12.

The particle counter 14 comprises means for automatic analysis of a fluid sample, means for storing the analysis results and means for transmitting the analysis data, preferably via a wireless system, but the data transmission may also be undertaken by means of cables.

Amongst other things, the automatic analysis equipment includes a laser diode 26 which passes light through a fluid sample 27. The light then passes from the laser 26 through a magnifying lens before being registered on an image sensor chip 29. The image registered on the image sensor chip 29 is then analysed by identification equipment 30 which identifies and counts particles displayed on the image. In the process relevant data are stored and transmitted, preferably wirelessly, to a receiver.

The particle counter also comprises a sample container 34 which can store a fluid sample removed from the pipe portion 12. This sample container 34 is releasably mounted in the particle counter 14 in such a manner that it is removed by an ROV or other mechanical equipment and transported to a laboratory for detailed analysis. This may be relevant, for example, if results transmitted from the automatic equipment for particle counting provide grounds for undertaking a more thorough analysis of the fluid sample. The particle counter may, of course, also be provided with more than one sample container 34.

In the pipe portion 12 is mounted a propeller unit 16. This unit is identical for the two embodiments and is illustrated in an enlarged version in FIGS. 2 and 4. The propeller unit 16 comprises a propeller 18 and a current-generating unit 20. Between the current-generating unit 20 and the particle counter 14 are mounted means 21, preferably electric cables, for transferring electric current to the particle counter.

For the first embodiment, as illustrated in FIG. 1, the propeller substantially has two main functions; firstly to create a pressure drop in the fluid in the pipe portion 12 between the fluid sample outlet 22 and the fluid return outlet 23, which is sufficient to drive fluid samples removed from the fluid flow in the pipe portion 12 through the particle counter 14 and back to the fluid flow in the pipe portion, and secondly to produce enough electric current to drive units and equipment in the particle counter which require electric current in order to function. This applies, for example, to the automatic analysis equipment.

In the second embodiment of the invention the propeller unit 16 is located slightly upstream of the fluid sample outlet 22. This prevents the creation of the pressure drop between the fluid sample outlet 22 and the fluid return outlet 23 necessary for driving the fluid samples through the particle counter 16 and back to the pipe portion 12. In the second embodiment, therefore, a pressure-reducing valve 24 is provided between the fluid sample outlet 22 and the fluid return outlet 23 to ensure that the pressure drop necessary for driving fluid samples through the particle counter and back to the pipe portion is created. Furthermore, the propeller unit in the second embodiment also produces sufficient electrical energy to run equipment in the particle counter which requires electrical energy in order to function in the same way as the first embodiment.

Thus both of the two embodiments of the invention are independent of the external supply of electric power since the pressure drop in the pipe flow causes the fluid samples to flow through the particle counter and back to the pipe flow without the use of a pump and since the electric power produced by the propeller unit 16 is sufficient to drive the particle counter.

The particle counter apparatus described above is particularly suitable for use in areas with difficult access, such as for example in bottom-based installations for production of hydrocarbons at sea. It is also suitable for use in areas where there is a risk of fire and explosion. In addition, the particle counter apparatus can, of course, be employed in areas with easy access and/or areas with no risk of fire or explosion.

Even though the present invention is described by means of two examples and with reference to possible embodiments, it should be understood that modifications or improvements may be carried out within the scope of the invention as defined by the attached patent claims. For example, it will be possible to also employ a pressure-reducing valve, as illustrated in connection with the embodiment in FIG. 3, in the embodiment of the invention where the propeller is mounted directly opposite the fluid sample outlet as illustrated in FIG. 1.

The invention claimed is:

1. A particle counter apparatus for counting particles in a fluid flowing in a pipe or a pipeline, which particle counter apparatus comprises a pipe portion through which the fluid flows, which pipe portion is provided with a fluid sample outlet for withdrawal of a fluid sample, which particle counter apparatus also comprises a first fluid transfer body extending from the fluid sample outlet to a particle counter, and a second fluid transfer body extending from the particle counter to a fluid return outlet mounted in the pipe portion downstream of the fluid sample outlet, wherein the particle counter apparatus further comprises a propeller unit with a propeller, which is mounted in the pipe portion, either directly opposite the fluid sample outlet or upstream of the fluid sample outlet, with the result that solid particles are distributed in the fluid before a fluid sample is withdrawn, which propeller further comprises a generator driven by the propeller and means for transmitting electrical energy to the particle counter, thereby enabling the propeller unit to supply the particle counter with sufficient electric power to operate the particle counter.

2. The particle counter apparatus according to claim 1, wherein the particle counter apparatus further comprises a pressure-reducing valve mounted in the pipeline between the first pipe branching and the second pipe branching, thereby permitting a pressure drop to be provided in the pipe flow which is sufficient to drive a fluid sample through the particle counter.

3. The particle counter apparatus according to claim 1, wherein the means for transmitting electric current produced from the propeller unit to the particle counter comprise electric cables.

4. The particle counter apparatus according to claim 1, wherein the fluid sample outlet comprises means for withdrawal of a predetermined amount of fluid.

5. The particle counter apparatus according to claim 4, wherein the means for withdrawal of a predetermined amount of fluid comprise at least one valve device.

6. The particle counter apparatus according to claim 5, wherein the at least one valve device is automatically controlled.

7. The particle counter apparatus according to claim 1, wherein the particle counter comprises means for automatic counting of particles in the fluid sample.

8. The particle counter apparatus according to claim 1, wherein the particle counter comprises a data storage unit which can store data concerning each individual fluid sample.

9. The particle counter apparatus according to claim 1, wherein the particle counter apparatus comprises means for transmitting data and/or control signals for controlling the particle counter apparatus between the particle counter apparatus and a receiver at a distance from the particle counter apparatus.

10. The particle counter apparatus according to claim 9, wherein the means for transmitting data and/or control signals comprise one or more devices for wireless transmission of data and/or control signals between the particle counter apparatus and the receiver.

11. The particle counter apparatus according to claim 9, wherein the means for transmitting data and/or control signals comprise one or more cables for transmitting data and/or control signals between the particle counter apparatus and the receiver.

12. The particle counter apparatus according to claim 1, wherein the particle counter comprises a sample container for collecting a fluid sample, thereby enabling the number of particles in the fluid sample to be counted in a suitable laboratory.

13. The particle counter apparatus according to claim 12, wherein the sample container is releasably mounted in the particle counter in such a manner that the sample container can be removed from and placed in the particle counter by an ROV, a robot or similar equipment.

14. The particle counter apparatus according to claim 1, wherein the fluid return outlet comprises means for preventing fluid flowing from the pipe portion into the second fluid transfer body.

15. The particle counter apparatus according to claim 1, wherein the pipe portion forms a part of a pipe or a pipeline for transport of a fluid.

16. A method for counting particles in the transport of fluid hydrocarbons in a pipe or a pipeline comprising passing the fluid hydrocarbons through the particle counter apparatus of claim 1, wherein the pipe portion of the apparatus forms a part of the pipe or the pipeline.

17. A method for counting particles in the transport of fluid hydrocarbons in a fluid pipe flow in a pipeline comprising passing the fluid pipe flow through the particle counter apparatus of claim 1, wherein the pipe portion of the apparatus is the pipeline and the pipeline is located under water or in an environment where there is a risk of fire and/or explosion.

* * * * *